(12) United States Patent
Hedner et al.

(10) Patent No.: US 7,981,443 B2
(45) Date of Patent: Jul. 19, 2011

(54) METHOD OF TREATING SLEEP DISORDERED BREATHING USING TOPIRAMATE

(76) Inventors: Jan Hedner, Göteborg (SE); Lars Sjöström, Hovås (SE); Kaj Stenlöf, Torslanda (SE); Ludger Grote, Göteborg (SE)

( * ) Notice: Subject to any disclaimer, the term of this patent is extended or adjusted under 35 U.S.C. 154(b) by 1518 days.

(21) Appl. No.: 10/204,048

(22) PCT Filed: Feb. 14, 2001

(86) PCT No.: PCT/SE01/00315
§ 371 (c)(1),
(2), (4) Date: Dec. 12, 2003

(87) PCT Pub. No.: WO01/62243
PCT Pub. Date: Aug. 30, 2001

(65) Prior Publication Data
US 2004/0082519 A1    Apr. 29, 2004

(30) Foreign Application Priority Data
Feb. 24, 2000  (SE) ...................................... 0000601

(51) Int. Cl.
| | |
|---|---|
| *A61K 9/20* | (2006.01) |
| *A61K 9/48* | (2006.01) |
| *A61K 9/16* | (2006.01) |
| *A61K 9/14* | (2006.01) |

(52) U.S. Cl. ........ 424/464; 424/465; 424/451; 424/490; 424/491; 424/488; 424/489

(58) Field of Classification Search .................. 424/464, 424/465, 451, 490, 491, 488, 489
See application file for complete search history.

(56) References Cited

U.S. PATENT DOCUMENTS

| | | |
|---|---|---|
| 4,513,006 A | 4/1985 | Maryanoff et al. |
| 7,056,890 B2 * | 6/2006 | Najarian ........................ 514/23 |

* cited by examiner

*Primary Examiner* — Isis A Ghali
(74) *Attorney, Agent, or Firm* — Dickstein Shapiro LLP

(57) ABSTRACT

A method for treating snoring, sleep apnoea and other forms of sleep disordered breathing involves administration to a patient of a therapeutically effective amount of topiramate over an appropriate period of time, such as a period substantially coinciding with the sleep period of a patient. A useful route of administration is per os. Also disclosed is the use of topiramate for the diagnosis of snoring, sleep apnoea and other forms of sleep disordered breathing.

10 Claims, No Drawings

METHOD OF TREATING SLEEP DISORDERED BREATHING USING TOPIRAMATE

FIELD OF THE INVENTION

The present invention relates to a method of treating and diagnosing sleep disordered breathing, especially obstructive sleep apnoea, and to means for carrying out said method.

BACKGROUND OF THE INVENTION

A patent upper airway is a basic requirement for breathing. This, of course, also holds true for breathing during sleep. It has recently been described that such patency—and thus breathing—may be partially or totally interrupted during sleep due to a collapse or obstruction of the upper airway; it should be observed that obstruction, in the context of the present invention, excludes obstruction by foreign objects or by material excreted by the body, such as mucus. In its simplest form partial airway collapse or obstruction is indicated by profound and vigorous snoring. More pronounced collapse or obstruction results in hypopnea, a condition in which airflow is reduced during inspiration with or without concomitant signs of hypoxemia. The condition of total collapse of the upper airway is referred to as obstructive sleep apnoea (OSA). This condition is associated with repeated episodes of interrupted airflow in spite of inspiratory attempts, resulting in hypoxemia, hemodynamic changes and arousal from sleep. Sleep fragmentation, hypoxia and/or other OSA phenomena yet unidentified are likely to lead to typical daytime symptoms such including hypersomnolence, cognitive disturbance, reduced working and driving performance, depression and loss of memory. Moreover, cardiovascular complications, in particular hypertension, cardiac failure, myocardial infarction and stroke are common in OSA and OSA has been associated with increased insulin resistance, diabetes, obesity, changes in lipid metabolism and increased platelet aggregability. Such symptoms and complications are not confined to severe cases but also observed in cases of partial OSA.

The prevalence of OSA in the adult population is in the order of 10-12%. The prevalence of OSA in combination with pronounced daytime symptoms in the order of 1-3%. The prevalence of minor daytime symptoms induced by discrete sleep-related breathing disturbances is unknown. However, habitual snoring is a common phenomenon reported by 15-25% of the adult population.

The patophysiology of OSA is virtually unknown. Though a number of predisposing factors have been identified, e.g. obesity, hypertrophied tissue in the upper airway (particularly in children), and short jaw, there is a large number of OSA prone individuals lacking these factors.

The absence of observable aberrant anatomic factors, however, does not exclude a dynamic malfunction of the tongue and the upper airway dilating musculature. Such defect function may originate in the central nervous system, at the level of signal transmission to peripheral muscles or at the neuromuscular junction. It is well known and has been reported in the literature that electromyographically recorded signal from the lingual muscles (submental EMG) may be attenuated or even disappear in association with obstructive apnoeas. This defective control seems to be particularly pronounced during sleep only, suggesting the central nervous, peripheral neural and/or neuromuscular control of the upper airway is particularly prone to be affected in this state.

The principal forms of treatment in OSA are surgery of the upper airway, intraoral mandibular advancement devices and long-term treatment with nasal continuous positive airway pressure (nCPAP). These methods of treatment are cumbersome and expensive. Various forms of pharmacological treatment, e.g. by administration of tricyclic anti-depressants, theophylline, progesterone, have been employed but have not gained wide clinical use.

OBJECTS OF THE INVENTION

As evident from the preceding description of the state of the art, there is a need for an improved method for treating snoring, sleep apnoea and other forms of sleep disordered breathing. In particular, pharmacological treatment of such disorders would offer a definite advantage over the invasive or non-invasive methods used at present, many of which only provide insufficient relief and some of which are cumbersome to the patient.

One object of the present invention thus is to provide a method for the treatment of snoring, sleep apnoea and other forms of sleep disordered breathing which reduces and/or eliminates some or all of the drawbacks of the methods known to the art.

Another object of the present invention is to provide a means for carrying out the method according to the invention.

A further object of the present invention is its application as a diagnostic tool for detecting the presence of OSA in a patient.

SUMMARY OF THE INVENTION

According to the present invention there is provided a method of treating snoring, sleep apnoea and other forms of sleep disordered breathing, all of them which included in the term OSA as used herein, said method comprising the administration of a pharmacologically active amount of topiramate. Topiramate, 2,3:4,5-di-o-isopropylidene-β-D-fructopyranose sulfamate (U.S. Pat. No. 4,513,006), a structurally novel compound, was first licensed in the UK in 1995 for adjunctive treatment in patients with intractable partial epilepsy. However, topiramate has not been considered for the treatment of snoring, sleep apnoea and other forms of sleep disordered breathing.

The pharmaceutical development and therapeutic use of topiramate has resulted in the gathering of substantial clinical experience specific to the compound. Most of that experience has been gained from trials as add-on therapy in patients with refractory partial epilepsy. However, topiramate has also been used in monotherapy of epilepsy and been shown to have substantial efficacy in children with Lennox-Gastaut syndrome, and patients with generalised tonic-clonic seizures. Due to its inherent activity to induce weight loss, an effect which at least in clinical practice appears to result from a lack of appetite, topiramate has been considered for clinical trials as an anti obesity agent. For a recent survey in respect of the therapeutic use of topiramate, see: S. D. Lhatoo and M. C. Walker, The safety and adverse event profile of topiramate, *Rev. Contemp. Pharmacother.* 1999; 10:185-91.

The positive effect of topiramate in the treatment of OSA related conditions may be due to one or more of the pharmacological actions exerted by topiramate in the central nervous system. A single action or several of these actions in concert may account for an increased drive in respiratory neurones in the medulla oblongata or an increased firing of neurones in the hypoglossal nucleus of the same area. Such an effect will cause increased muscular tone of the upper airway muscles during sleep and thereby reduce snoring, sleep apnoea and other forms of sleep disordered breathing (OSA). While these hypotheses provide scientifically attractive explanations for the observed effect of topiramate in the conditions which the present invention seeks to treat, it must be emphasised that they must not be considered to be binding in any way on the concept and the working of the present invention. Previous neurochemical and neurophysiological studies have revealed evidence that the action of topiramate in the central nervous system includes a modulation of sodium and/or calcium channel conductance whereby topiramate has been shown to dose-dependently reduce cellular activity and depress cellular bursting activity by a specific action on voltage-gated sodium electrogenesis in certain areas of the nervous system. Although this action, providing in involves brain stem neurones, apparently would reduce activity in the hypoglossus nucleus its is also possible that it may act to stabilise premature and desynchronised bursting which occurs in these cells out of phase with the breathing pattern. A second and potentially related effect of topiramate is its capacity to potentiate GABA-mediated effects by a possible direct modulatory action, not mediated via direct receptor binding, on the GABA-A receptor complex. GABA activity has not been investigated in sleep apneics. Hypoxia has been experimentally proven to increase GABA activity in several experimental models. Other experiments have shown that GABA may reduce respiratory drive after application in the central nervous system. It may be speculated that hypoxia, such as occurs in association with obstructive apneas during sleep, acts to inhibit respiration via a GABA mediated mechanism which in turn may be attenuated by topiramate. A similar mechanism may apply to the third property of topiramate which relates to its glutamate antagonistic effect. Topiramate has been shown to reduce abnormally high concentrations of glutamate in the hippocampus. Other studies have demonstrated that topiramate blocked the kainate-elicited excitatory response in rat hippocampal pyramidal neurones by an effect at the aminohydroxymethylisoxazole propionic acid (AMPA) glutamate receptor subtype site, but had no effect at the N-methyl-D-aspartate (NMDA) mediated glutamate receptor subtype site. Hypoxia is known to elevate glutamate production and activity in the brain. The potential adverse effects of this mechanism on central respiratory regulation in OSA may be reduced by topiramate. Finally, topiramate has been demonstrated to weakly inhibit the enzyme carbonic anhydrase, an effect which would tend to shift the metabolic acid-base balance towards acidosis. Acidosis, such as induced by e.g. administration of carbon dioxide to patients with OSA, has been shown to partly eliminate apnoeas. Although high carbon dioxide breathing is generally associated with an arousal from sleep, weak carbonic anhydrase inhibition by topiramate may create a balanced stimulus for increased respiratory drive and thereby a beneficial effect without arousal in patients with OSA.

An effective amount of topiramate is one which eliminates or substantially reduces the manifestations of OSA-related conditions over a period of sleep, such as sleep periods from 10 minutes to 10 hours.

Topiramate is advantageously formulated in a way appropriate to the chosen administration route.

Topiramate may administered by various routes. The most preferred route is by peroral administration whereby topiramate absorption will be directed to the gastrointestinal tract. The compound of the invention may also be incorporated in tablets, lozenges, capsules or similar, in particular solid pharmaceutical preparations designed for preferred uptake of the compound through the oral mucosa. Pharmaceutical compositions may be adapted to such absorption which is of particular interest. Knowledge about clinical pharmacokinetics of topiramate (see, for instance: R P Shank, J F Gardocki, J L Vaught et al., Topiramate: preclinical evaluation of a structurally novel anticonvulsant. *Epilepsia* 1994; 35: 450-60) is useful in designing topiramate preparations for administration to a patient. For this purpose formulation techniques known in the art may be used. In this context reference is made to Pharmaceutical Dosage Forms: Tablets. Vol. 1-3, H A Lieberman et al., Eds. Marcel Dekker, New York and Basel, 1989-1990, which hereby is incorporated into this application by reference. In particular specific reference is made to chapter 7 (Special Tablets, by J W Conine and M J Pikal), chapter 8 (Chewable Tablets, by R W Mendes, O A Anaebonam and J B Daruwala), and chapter 9 (Medicated Lozenges; by D Peters).

The amount of topiramate to be administered for treatment of sleep disordered breathing will vary depending on factors such as the particular formulation of topiramate used, the route of administration, the release profile of the formulation into which it is incorporated, the severity of the disease, individual pharmacokinetic and dynamic properties as well as the status of the patient. For instance, the dose range for peroral administration of topiramate will be in the interval from 10 to 1000 mg per 24 hours. Normally, an amount of from 100 to 400 mg of topiramate is envisaged as the normal range used for a peroral administration in OSA. The appropriate dose range for the compound can be determined by titration in routine experiments.

In addition to the methods of administration of the compound of the invention mentioned above also parenteral, intranasal, and rectal administration is useful, as well as administration by inhalation or transdermal administration. The transdermal formulation is specifically advantageous in regard of simplicity and from a patient comfort standpoint. In this case, the agent is applied to the skin in form of a viscous ointment or similar. Transdermal systems (patches provided with a liquid or semi-liquid pharmaceutical composition) for controlled drug delivery through the skin are well known in the art, for instance for the administration of nicotine and drugs used for diseases of the circulatory system.

The timing of the administration of topiramate according to the invention will depend on the formulation and/or route of administration used. Typically, administration of topiramate will, in the majority of cases, be given as a long-term treatment regimen whereby pharmacokinetic steady state conditions will be reached. Medication for peroral or parenteral administration may also be given in immediate relation to a particular sleeping period, for instance 10 minutes to 3 hours prior to the onset of sleep.

According to the invention topiramate may also be combined, in one and the same pharmaceutical preparation, with other pharmacologically active compounds useful in the treatment of OSA.

According to the invention topiramate may also be used for diagnosing sleep disorders related to snoring, sleep apnoea or other forms of sleep disordered breathing to dissociate them from other types of sleep disorders. The diagnostic method according to the invention comprises administration to the patient topiramate in increasing amounts prior to or during a series of sleep episodes; administration can be in single or multiple doses. The observation of a reduction of the severity and/or number of sleep disordered breathing events or reduced daytime sleepiness/increased alertness is indicative of the presence of obstructive sleep apnoea.

The invention will now be explained in more detail by reference to a preferred but not limiting embodiment showing the effect of topiramate on sleep disordered breathing in two patients with light to moderate OSA.

DESCRIPTION OF A PREFERRED EMBODIMENT

Example. Double-blind, Placebo Controlled Cross-over Study with Topiramate

A double-blind, placebo controlled cross-over study of topiramate was undertaken in 2 patients with light to moderate OSA (A/H index, 22 and 35 on previous screening). Topiramate (100 mg b.i.d or corresponding placebo) was administered for 10 days in each cross-over period. A washout period of one week was applied between the two treatment periods. A/H index during placebo (24 and 33) was reduced (to 9 and 6, respectively) during topiramate. The most pronounced relative reduction was seen in the second patient which also had the most pronounced hypoxia (minimum saturation level 74% compared to 85%) during the night on placebo. Daytime sleepiness was markedly reduced as evidenced by spontaneous reporting by both patients. Blood pressure did not differ between the two study nights as was the body mass index (BMI; 29.5 and 30.3 in the two patients). There was no clinically significant change in total sleep time after topiramate and the relative proportions of non-REM stage 1+2 and slow wave sleep as well as REM sleep remained unchanged. No side effects were reported during the study period.

These findings demonstrate a potent apnoea reducing effect of topiramate in sleep apneics. Moreover, the study suggests that a beneficial effect in sleep apnoea may be maintained over a more extended time period.

The study of OSA in animal models or in healthy persons (OSA then induced by artificial means) may lack relevance for patients in which the pathophysiological mechanism affected by topiramate is acquired or genetically determined.

The invention claimed is:

1. A method for treating sleep disordered breathing consisting of peroral administration to a patient a therapeutically effective dose of an active agent consisting of topiramate.

2. The method of claim 1, wherein said therapeutically effective dose is effective during a substantial portion of a single sleep period.

3. The method of claim 2, wherein said substantial portion is 50% or more.

4. The method of claim 2, wherein said substantial portion is 80% or more.

5. The method of claim 2, wherein said single sleep period is from one to eight hours.

6. The method of claim 1, wherein the therapeutically active dose is released from a composition for controlled release.

7. The method of claim 6, wherein from 50% to 100% of the therapeutically effective dose is released within a period of three hours from administration.

8. The method of claim 6, wherein from 80% to 100% of the therapeutically effective dose is released within a period of five hours from administration.

9. The method of claim 1, wherein said therapeutically effective dose is from 10 to 1000 mg.

10. The method of claim 1, wherein said sleep disordered breathing is sleep apnoea and said therapeutically effective dose is an apnoea reducing amount.

* * * * *